United States Patent [19]

Poblet et al.

[11] Patent Number: 5,527,881

[45] Date of Patent: Jun. 18, 1996

[54] PROCEDURE FOR PREPARING SALMON CALCITONIN

[75] Inventors: Marcos C. Poblet; Berta P. Obiols; Gemma J. Farres, all of Barcelona, Spain

[73] Assignee: Lipotec, S.A., Spain

[21] Appl. No.: 164,408

[22] Filed: Dec. 9, 1993

[30] Foreign Application Priority Data

Dec. 10, 1992 [ES] Spain .................................. 9202510

[51] Int. Cl.$^6$ .................................................. A61K 38/23
[52] U.S. Cl. ........................ 530/307; 530/326; 530/328; 530/334; 530/336; 530/324; 525/54.1
[58] Field of Search ........................ 514/13, 15; 530/307, 530/324, 327, 328, 334, 336, 326; 525/54.1

[56] References Cited

U.S. PATENT DOCUMENTS

| | | | |
|---|---|---|---|
| 3,891,614 | 6/1975 | Sakakibara et al. | 260/112.5 |
| 3,988,309 | 10/1976 | Matsuda et al. | 260/112.5 T |
| 4,159,981 | 7/1979 | Rittel et al. | 260/112.55 |
| 4,804,742 | 2/1989 | Neiss et al. | 530/307 |
| 5,162,305 | 11/1992 | Fujii et al. | 514/12 |
| 5,175,146 | 12/1992 | Basava et al. | 514/12 |

FOREIGN PATENT DOCUMENTS

0529075A1  10/1991  European Pat. Off. .

OTHER PUBLICATIONS

Pepitides 1990, Proceedings of the 21st European Peptide Symposium, pp. 131–133.
"Solid phase synthesis of partially protected and free peptides containing disulphide bonds by simultaneous cysteine oxidation–release from 2-chlorotrityl resin," Barlos et al., Int'l. J. of Peptide & Protein Research, vol. 38, No. 6, 1991, pp. 562–568.
"Solid phase peptide synthesis utilizing 9–fluorenylmethoxycarbonyl amino acids," Fields et al., Int'l. J. of Peptide & Protein Research, vol. 35, No. 3, 1990, pp. 161–214.
Guttman et al. Calcitonin 1969. Proc. 2nd Int. Symposium (21–24 Jul. 1969) pp. 74–79.
Albericio et al. J. Org. Chem. vol. 55 p. 3730 (1990).
Atherlon et al. J. Am. Chem. Soc. vol. 97, p. 6584 (1975).
Barany et al. Int. J. Pept. Prot. Res. vol. 30 p. 705. (1987).

Primary Examiner—Christina Y. Chan
Assistant Examiner—David Lukton
Attorney, Agent, or Firm—Wigman, Cohen, Leitner & Myers

[57] ABSTRACT

A procedure for the preparation of salmon calcitonin comprising the condensation of fragment 1(SEQ ID NO: 1), a docosapeptide corresponding to the carboxamide end of the salmon calcitonin sequence conveniently protected and anchored on resin, with fragment 2(SEQ ID NO:2), a decapeptide corresponding to the amino end of the salmon calcitonin sequence conveniently protected and with a disulphide bridge ready formed between the two cysteines, and the treatment of the complete peptide skeleton (fragment 6 (SEQ ID NO:6)) with an acid to liberate the totally deprotected peptide from the resin.

Lys(Boc)—Leu—Ser(tBu)—Gln—Glu(tBu)—Leu—His(Trt)—

Lys(Boc)—Leu—Gln—Thr(tBu)—Tyr(tBu)—Pro—Arg(Pmc)—

Thr(tBu)—Asn—Thr(tBu)—Gly—Ser(tBu)—Gly—Thr(tBu)—Pro—(R)

Fragment 1

Boc—Cys—Ser(tBu)—Asn—Leu—Ser(tBu)—Thr(tBu)—Cys—Val—

—Leu—Gly—OH

Fragment 2

Boc—Cys—Ser(tBu)—Asn—Leu—Ser(tBu)—Thr(tBu)—Cys—Val—

—Leu—Gly—Lys(Boc)—Leu—Ser(tBu)—Gln—Glu(tBu)—Leu—

—His(Trt)—Lys(Boc)

Leu—Gln—Thr(tBu)—Tyr(tBu)—Pro—Arg(Pmc)—Thr(tBu)—

—Asn—Thr(tBu)—Gly—Ser(tBu)—Gly—Thr(tBu)—Pro—(R)

Fragment 6

13 Claims, No Drawings

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH:22 amino acids
        ( B ) TYPE:amino acid
        ( C ) TOPOLOGY:linear ( i i ) MOLECULE TYPE:protein ( v ) FRAGMENT TYPE:C-Terminal type ( i x ) FEATURE:
        ( D ) OTHER INFORMATION:Lys position 1 substituted with
            - 6 t- butoxycarbonyl
            Ser at position 3 substituted with
            tert- butyl
            Glu at position 5 substituted with
            tert- butyl
            His at position 7 substituted with
            trityl
            Lys at position 8 substituted with
            t- butoxycarbonyl
            Thr at position 11 substituted with
            tert- butyl
            Tyr at position 12 substituted with
            tert- butyl
            Arg at position 14 substituted with
            2,2,5,7,8- pentamethylchroman-6-sulphonyl
            Thr at position 15 substituted with
            tert- butyl
            Thr at position 17 substituted with
            tert- butyl
            Ser at position 19 substituted with
            tert- butyl
            Thr at position 21 substituted with
            tert- butyl ( x i ) SEQUENCE DESCRIPTION: SEQ ID NO:1:

```
Lys  Leu  Ser  Gln  Glu  Leu  His  Lys  Leu  Gln  Thr  Tyr  Pro  Arg  Thr  Asn
 1                  5                        10                            15
Thr  Gly  Ser  Gly  Thr  Pro
                20
```

( 2 ) INFORMATION FOR SEQ ID NO:2:

( i ) SEQUENCE CHARACTERISTICS:
        ( A ) LENGTH:10 amino acids
        ( B ) TYPE:amino acid
        ( D ) TOPOLOGY:linear ( i i ) MOLECULE TYPE:protein ( v ) FRAGMENT TYPE:N-terminal ( i x ) FEATURE:
        ( D ) OTHER INFORMATION: Ser at position 2 substituted
            with tert- butyl
            Ser at position 5 substituted with tert-butyl
            Thr at position 6 substituted with tert-butyl ( x i ) SEQUENCE DESCRIPTION: SEQ ID NO: 2:

```
Cys  Ser  Asn  Leu  Ser  Thr  Cys  Val  Leu  Gly
 1                  5                        10
```

( 2 ) INFORMATION FOR SEQ ID NO:3:

( i ) SEQUENCE CHARACTERISTICS:
    ( A ) LENGTH:10 amino acids
    ( B ) TYPE:amino acid
    ( D ) TOPOLOGY:linear ( i i ) MOLECULE TYPE:protein ( v ) FRAGMENT TYPE:

( i x ) FEATURE:N-Terminal
    ( D ) OTHER INFORMATION: Cys in position 1 substituted
        with acetamidomethyl
        Ser in position 2 substituted with
        tert- butyl
        Thr in position 6 substituted with
        tert- butyl
        Cys in position 7 substituted with
        trityl ( x i ) SEQUENCE DESCRIPTION: SEQ ID NO:3:

Cys Ser Asn Leu Ser Thr Cys Val Leu Gly
 1            5                    10

( 2 ) INFORMATION FOR SEQ ID NO:4:

( i ) SEQUENCE CHARACTERISTICS:
        ( A ) LENGTH:10 amino acids
        ( B ) TYPE:amino acid
        ( D ) TOPOLOGY:linear ( i i ) MOLECULE TYPE:protein ( i x ) FEATURE:
        ( D ) OTHER INFORMATION: Cys at position 1 substituted
            with acetamidomethyl
            Ser at position 2 substituted with tert-butyl
            Ser at position 5 substituted with tert-butyl
            Thr at position 6 substituted with tert-butyl
            Cys at position 7 substituted with trityl ( x i ) SEQUENCE DESCRIPTION: SEQ ID NO:4:

Cys Ser Asn Leu Ser Thr Cys Val Leu Gly
 1            5                    10

( 2 ) INFORMATION FOR SEQ ID NO:5:

( i ) SEQUENCE CHARACTERISTICS:
        ( A ) LENGTH:10 amino acids
        ( B ) TYPE:amino acid
        ( D ) TOPOLOGY:linear ( i i ) MOLECULE TYPE:protein ( i x ) FEATURE:
        ( D ) OTHER INFORMATION: Ser at position 3
            substituted with tert-butyl
            Ser at position 6 substituted with tert-butyl
            Thr at position 7 substituted with tert-butyl ( x i ) SEQUENCE DESCRIPTION: SEQ ID NO:5:

Cys Ser Asn Leu Ser Thr Cys Val Leu Gly
 1            5                    10

( 2 ) INFORMATION FOR SEQ ID NO:6:

( i ) SEQUENCE CHARACTERISTICS:
        ( A ) LENGTH:32 amino acids
        ( B ) TYPE:amino acid
        ( D ) TOPOLOGY:linear ( i i ) MOLECULE TYPE:protein ( i x ) FEATURE:

(D) OTHER INFORMATION: Ser at position 2 substituted
with tert- butyl
Ser at position 5 substituted with tert-butyl
Tyr at position 4 substituted with tert-butyl
Arg at position 6 substituted with tert-butyl
Thr at position 6 substituted with tert-butyl
Lys at position 11 substituted with tert-butyl
Ser at position 13 substituted with tert-butyl
Glu at position 15 substituted with tert-butyl
His at position 17 substituted with trityl
Lys at position 18 substituted with t-butoxycarbonyl
Thr at position 21 substituted with tert-butyl
Tyr at position 22 substituted with tert-butyl
Arg at position 24 substituted with
2,2,5,7,8- pentamethylchroman-6-sulphonyl
Thr at position 25 substituted with tert-butyl
Thr at position 27 substituted with tert-butyl
Ser at position 29 substituted with tert-butyl
Thr at position 31 substituted with tert-butyl (xi) SEQUENCE DESCRIPTION: SEQ ID NO:6:

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

(2) INFORMATION FOR SEQ ID NO:7:

(i) SEQUENCE CHARACTERISTICS:
(A) LENGTH:32 amino acids
(B) TYPE:amino acid
(D) TOPOLOGY:linear (ii) MOLECULE TYPE:protein (ix) FEATURE:
(D) OTHER INFORMATION: Ser at position 5 substituted
with tert- butyl
Thr at position 6 substituted with tert-butyl
Cys at position 7 substituted with trityl
Lys at position 11 substituted with t-butoxycarbonyl
Ser at position 13 substituted with tert-butyl
Glu at position 15 substituted with tert-butyl
His at position 17 substituted with trityl
Lys at position 18 substituted with trityl
Thr at position 21 substituted with tert-butyl
Tyr at position 22 substituted with tert-butyl
Arg at position 24 substituted with
2,2,5,7,8- pentamethylcroman-6-sulphonyl
Thr at position 25 substituted with tert-butyl
Thr at position 27 substituted with tert-butyl
Ser at position 29 substituted with tert-butyl
Thr at position 31 substituted with tert-butyl (xi) SEQUENCE DESCRIPTION: SEQ ID NO:7:

Cys Ser Asn Leu Ser Thr Cys Val Leu Gly Lys Leu Ser Gln Glu
1               5                   10                  15

Leu His Lys Leu Gln Thr Tyr Pro Arg Thr Asn Thr Gly Ser Gly
            20                  25                  30

Thr Pro

PROCEDURE FOR PREPARING SALMON CALCITONIN

The present invention relates to a procedure for the preparation of salmon calcitonin and all of its pharmaceutically acceptable salts formed by acid addition or complexes thereof. The invention further relates to the preparation of intermediate compounds which are useful in the synthesis of salmon calcitonin according to the invention.

BACKGROUND OF THE INVENTION

Salmon calcitonin is a natural peptide hormone extracted from said animal and which is 40 times more active than human calcitonin, a hormone with an essentially similar structure secreted mainly by the parafollicular cells of the thyroid in order to regulate the level and distribution of intra and extracellular calcium. Both human and salmon calcitonin have therapeutic applications in the prevention of senile and post menopause osteoporosis, as well for patients suffering from Paget's disease.

Many ways of obtaining calcitonins (human, salmon, eel, porcine, etc.) have been described in the past, for example by extracting tissue from the-various species, by DNA recombination techniques and by chemical synthesis.

Thus, salmon calcitonin can be obtained by extraction from the bronchial glands of said animal. Nevertheless, the low yield of active extract produced by this process has lead to the search for means ,of synthesizing it as an alternative to extraction.

Among the methods of obtaining calcitonin by chemical synthesis, and in parallel with the advances in the synthesis of peptides and proteins, chemical methodologies in solution and in the solid phase have been described.

The synthesis of salmon calcitonin by means of a classical strategy of peptide synthesis was described in 1969 by Guttman Set el. al. (HELV.; Chim. Acta52, 1789–1795). The innovation of solid ,phase synthesis processes in the field of peptide synthesis, the introduction of new orthogonal combinations of protective groups and new supports, together with the strategy of convergent synthesis, have opened up new possibilities in the procedures for obtaining calcitonin.

Until now various solid phase synthesis procedures for obtaining calcitonin (human, porcine, bovine, salmon, eel, etc.) have been mentioned in the U.S. Pat. Nos. 3,926,938 and 3,891,614 as well as in the articles by Kamber. B, Riniker. B, Peptides: Chemistry and Biology, pp. 525–6 (Smith J. A., Rivier J. E. Eds) 1992 ESCOM Science Publishers, basically using Boc/Bzl type protection strategies (Barney G., Merrifield R. B., (1980) The Peptides (Gross E., Melenhofer J. Eds) vol. 2 pp 1–284, Academic Press, New York), both in convergent synthesis schemes (Pedroso et al. Tetrahedron (1982), 38, 1183) (the Joining of two or more fragments) and in linear synthesis processes (the Joining of the 32 amino acids one by one). In general the use of Boc/Bzl derivatives implies a high yield cost both in the processes of synthesis related to the strong deprotection conditions, and consequently the elaborate purification processes.

DESCRIPTION OF THE INVENTION

The present invention is based on investigations into the solid phase synthesis of calcitonin using the methodology known as soft conditions, based on the use of Fmoc/t-Bu type protection which requires softer deprotection conditions, either with linear or convergent synthesis protocols, i.e. by the condensation of complementary fragments in solution or in the solid phase.

Some examples of solid phase synthesis with Fmoc/t-Bu type protection can be found in recent literature.

Surprisingly it has now been found that, after the liberation/deprotection of the complete peptide skeleton, the strategy of convergent synthesis by means of the condensation of Fragments 1 and 2 or 3 (SEQ ID NOS: 1 and 2 or 3) (Diagrams 1 and 2 below) leads to a reaction crude with a high yield of calcitonin, which means that not only is the purification process simplified but the yields of other processes described are increased.

The present invention therefore provides a new procedure for solid phase synthesis with new polymeric supports and a new synthesis methodology using protective groups combined with the convergent strategy.

In particular, the present invention provides a procedure for obtaining salmon calcitonin, a peptide hormone comprising 32 sequential amino acids, based on solid phase synthesis using Fmoc/t-Bu type protective group methodology (on convenient functionalized supports) combined with a convergent strategy, all according to the following diagram:

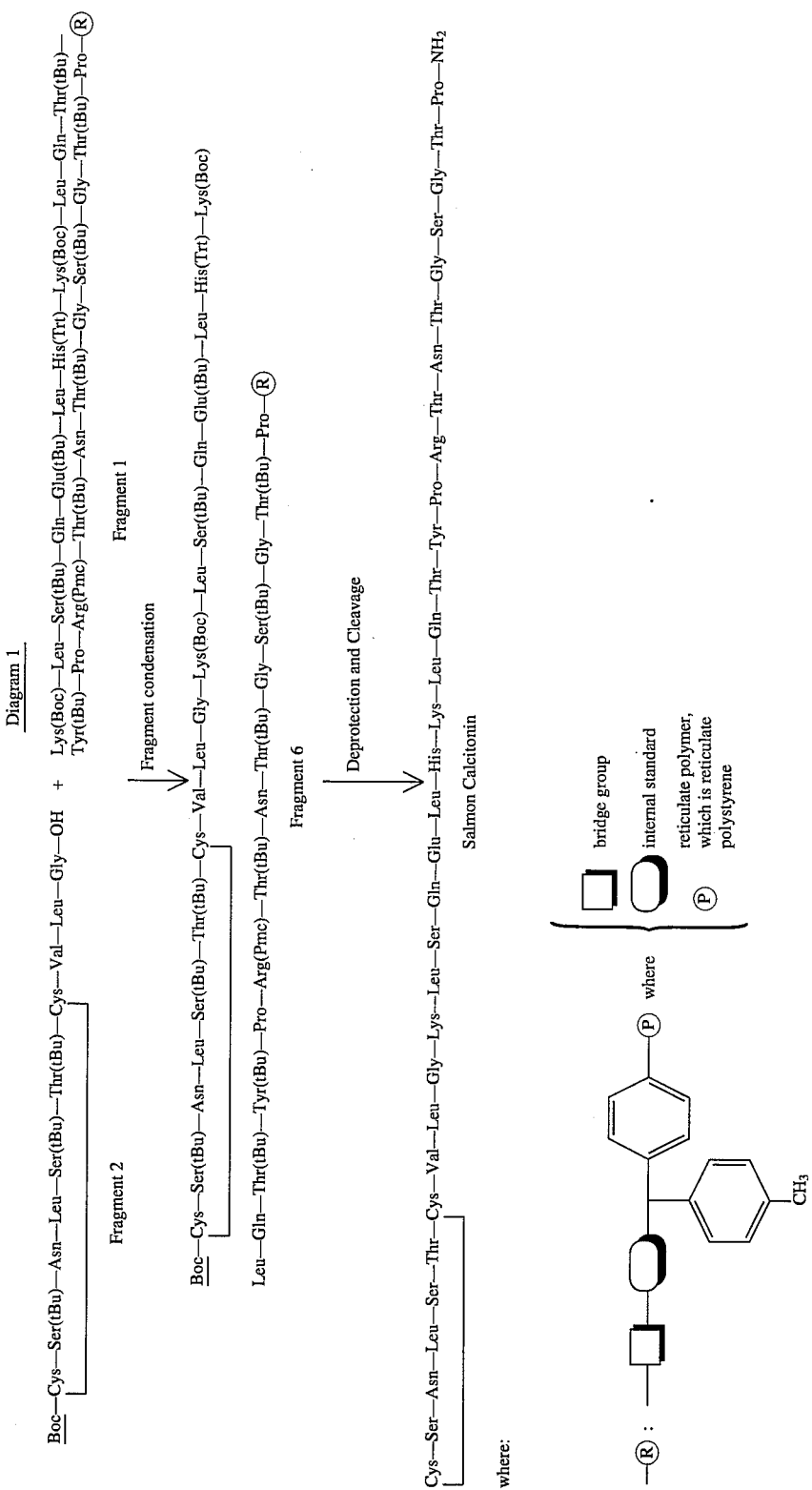

As shown, Ⓡ refers to the Ⓡ of diagram 1, namely the solid support and the bridge groups having the structure shown after the colon.

Referring to the previous diagram 1, the procedure of the invention consists of the condensation of fragment 1, (SEQ ID NO:1) a docosapeptide corresponding to the carboxamide end of the salmon calcitonin sequence, conveniently protected and anchored on resin, with fragment 2(SEQ ID NO:2), a decapeptide corresponding to the amino end of the salmon calcitonin sequence, conveniently protected and with a disulphide bridge ready formed between the two cysteines.

Once the complete peptide skeleton (fragment 6(SEQ ID NO:6) has been constructed the peptide is cleaved from the resin and totally deprotected, already in its oxide form, by means of an acid treatment. Finally, after subsequent purification chemically pure salmon calcitonin is obtained.

In particular, the condensation of fragment 1 with fragment 2 (diagram 1(SEQ ID NO:2)) which leads to fragment 6 (SEQ ID NO:6) (not described previously by literature) is carried out by the conventional methods of solid phase synthesis which have already been described. Once condensation is complete, the peptide-resin is subjected to a simultaneous process of deprotection of the side chains and de-anchoring the resin using 95% trifluoroacetic acid in the presence of scavengers. The resulting crude is purified by high pressure liquid chromatography. All of the homogeneous fractions are combined and are freeze-dried, thereby obtaining chemically pure salmon calcitonin.

According to another modality, the procedure of the invention may be carried out according to the following diagram 2:

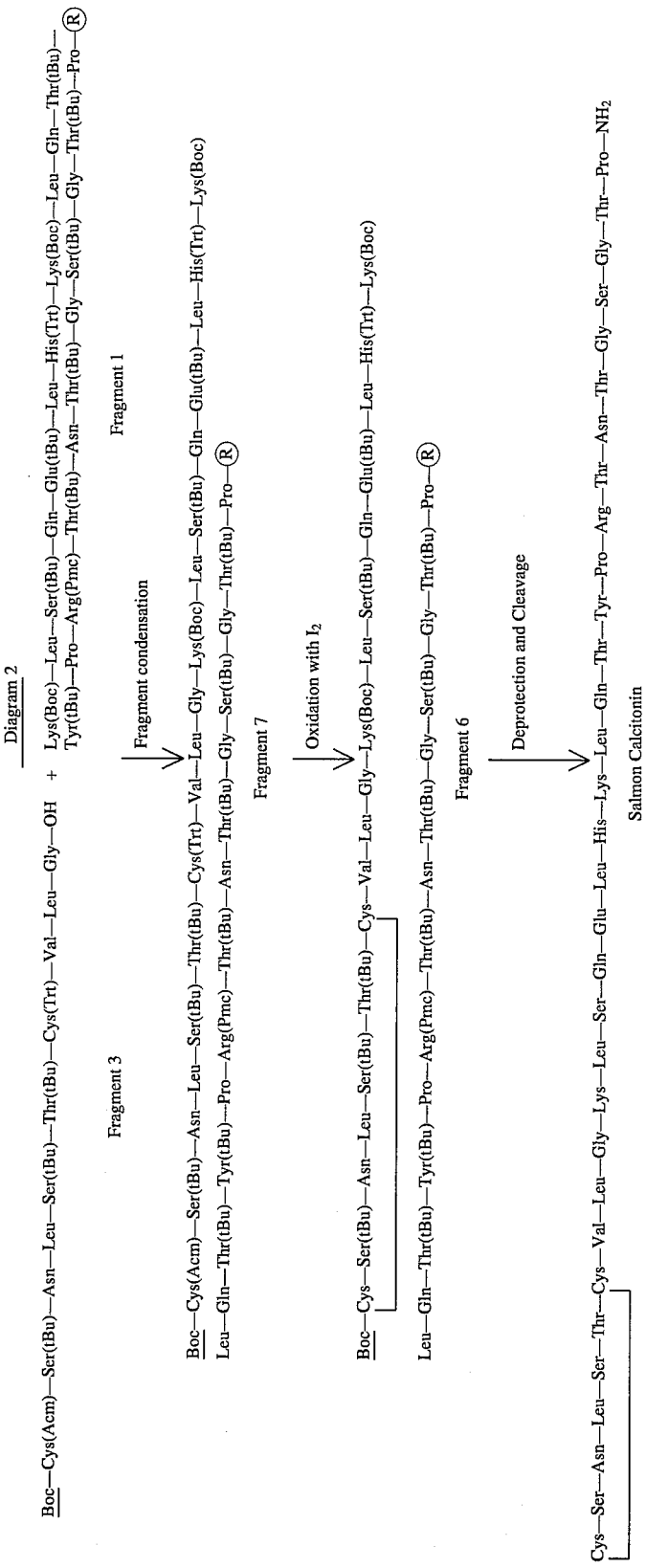

where R is defined as before in diagram 1 and structure of Ⓡ shown immediately after diagram 1 wherein Ⓡ is an abbreviation for the solid support and bridge groups.

According to diagram 2, fragment 1 (SEQ ID NO:1) is condensed with fragment 3(SEQ ID NO: 2), the precursor of fragment 2(SEQ ID NO:2), and then the disulphide bride is formed between the two cysteines (fragment 7(SEQ ID NO: 7)) by a solid phase selective oxidation reaction. Finally, once the peptide structure is complete in its oxidized form (fragment 6(SEQ ID NO: 6)) (with the disulphide bridge between the two cysteines) the deprotection of the remaining protective groups and liberation from the resin is the bridge group or handle which is incorporated is [1-(9H-fluoren-9 -yl)methoxy-formamide]methyl-3,5-dimethoxyphenoxyvaleric acid (Fmoc-PAL) (Albericio et al. J.Org. Chem. (1990), 55, 3730) or alternatively p-[(R,S)-a-[1-(9H-fluoren-9-yl)methoxy -formamide]-2,4-dimethoxy benzyl]-phenoxy acetic acid (Fmoc-AM) (Atherton et al. J. Am. Chem. Soc, (1975), 97,6584. The incorporation of the bridge group is followed by linear synthesis, residuum by residuum, until the 22 amino acids have been incorporated, using Fmoc as the protective group for the amino end in all cases. For the side chains Lys, Ser, Thr, Tyr, Arg, Glu, His, Gln and Asn, the protective groups are those indicated in the following FIG. 3:

Diagram 3

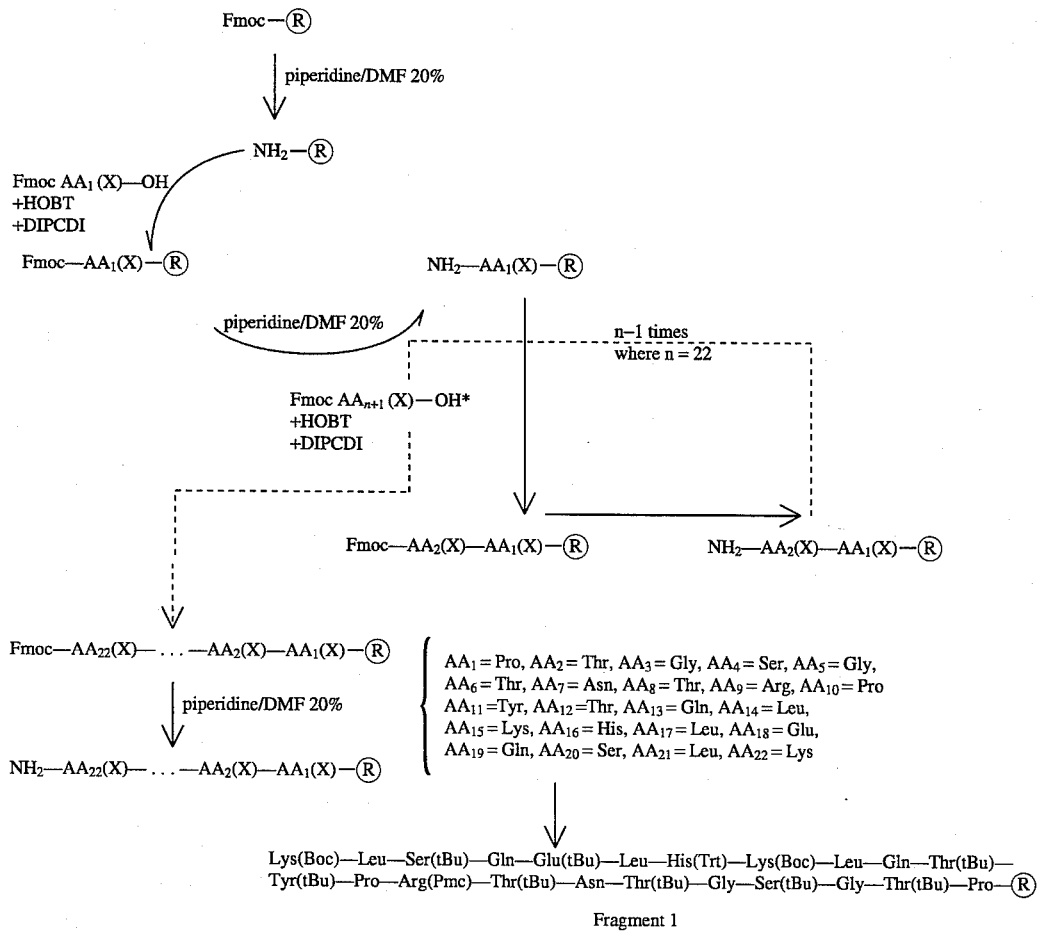

Fragment 1 carried out. After conventional purification, chemically pure salmon calcitonin is thus obtained.

According to another aspect and as mentioned above, the invention also provides a procedure for obtaining said fragment 1(SEQ ID NO:1), as well as a procedure for obtaining fragment 2(SEQ ID NO:2) and its precursor fragment 3(SEQ ID NO:3) and other fragments, all of them used in diagrams 1 and 2 above for the preparation of salmon calcitonin according to the present invention.

Fragments 1 and 2 (SEQ ID NO:2) are obtained starting with paramethylbenzhydrilamine resin (pMBHA) and incorporating an internal standard and a bridge group (handle) between the resin and the amino acids of the respective sequences.

To obtain fragment 1(SEQ ID NO:1), and because the terminal carboxy end of salmon calcitonin is a carboxamide, where R is defined as before in diagram 1 and the structure of —Ⓡ shown immediately after diagram 1.

To obtain fragment 2(SEQ ID NO:2), and because the terminal carboxy end must be carboxyacid, the bridge group or handle incorporated is 4(4-hydroxymethyl-3-methoxyphenoxy)butyric acid known as the Riniker Handle (}IMP.B) (Florsheimer et al.). The incorporation of bridge group is followed by linear synthesis, residuum by residuum, until the ten amino acids have been incorporated, using Fmoc as the protective group for the amino end in all cases except the last amino acid, for which the Boc group is used. For the protection of the side chains Ser, Thr, Asn, Cys the groups tBU, Trt or Acm are used respectively obtaining fragment 4(SEQ ID NO:4), not previously described by literature, as indicated in the following diagram 4:

Diagram 4
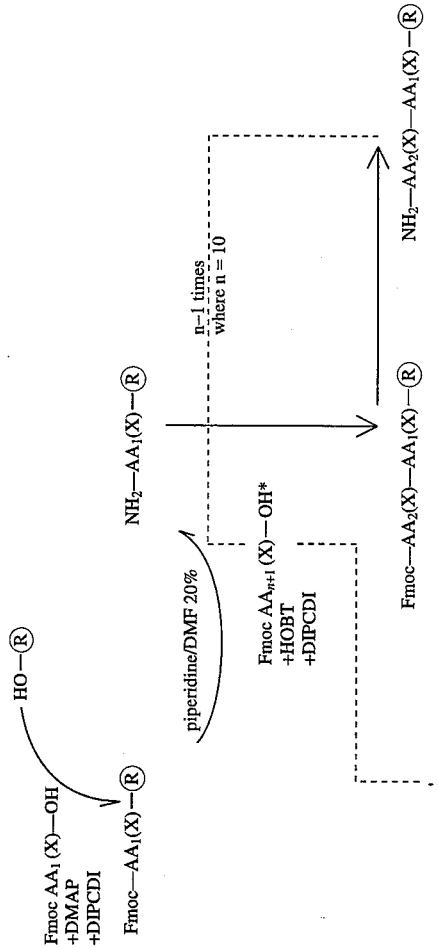
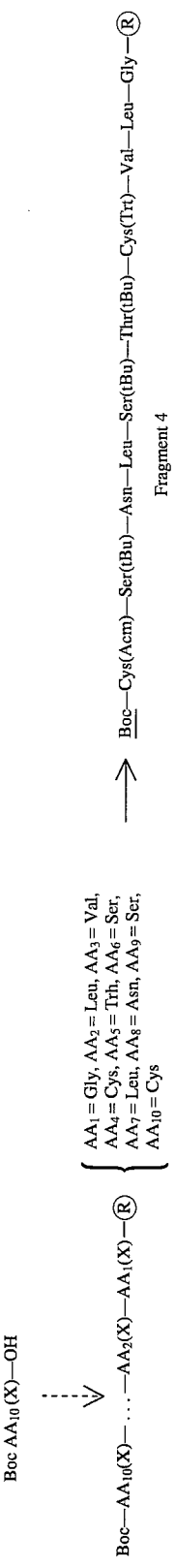

-continued
Diagram 4

Boc—Cys—Ser(tBu)—Asn—Leu—Ser(tBu)—Thr(tBu)—Cys—Val—Leu—Gly

Fragment 2

The simultaneous deprotection/oxidation with iodine of the two protective groups of the cysteine residua (Acm and Trt) respectively, leads to fragment 5(SEQ ID NO:5), not previously described in literature, with a high yield and a high degree of purity. Finally, by breaking the peptide-resin bond with trifluoroacetic acid in 1% dichloromethane, fragment 2 (SEQ ID NO:2) is produced.

Alternatively, referring again to diagram 4, by breaking the peptide-resin link of fragment 4(SEQ ID NO:4) fragment 3(SEQ ID NO:3) is obtained, a product not previously described by literature and which, by oxidation with iodine, can in turn lead to fragment 2(SEQ ID NO:2).

The abbreviations used in the present description have the following meanings:

Acm: acetamidomethyl
AcOH: acetic acid
AM: p-[(R,S)-2,4-dimethoxy benzyl]-phenoxy acetic
Arg: L-arginine
Asn: L-asparagine
Boc: t-butoxycarbonyl
Bzl: benzyl
Cis: cystine
Cys: cysteine
DCM: dichloromethane
DMF: N,N'-dimethylformamide
DIEA: N,N'-diisopropylethyl amine
DIPCDI: diiosopropylcarbodiimide
DMAP: dimethylamtnopyridine
Fmoc: 9-fluorenylmethoxycarbonyl
Gln: L-glutamine
Glu: L-glutamic acid
Gly: L-glycine
HBTU : O -(benzotriazole-1-yl)-N,N,N',N'-tetramethyluronide hexafluorophosphate
His: L-histidine
HMPB: 4(4-hydroxymethyl-3-methoxyphenoxy)butyric acid
HOBT: N-hydroxybenzotriazole
HPLC: high pressure liquid chromatography
Leu: L-leucine
Lys: L-lysine
Meb: p-methylbenzyl
Mtr: methoxytrityl
MPLC: medium pressure liquid chromatography
PAL: aminomethyl-3,5-dimethoxyphenoxyvaleric acid
pMBHA: para-methylbenzhydrilamine
Pmc: 2,2,5,7,8-pentamethylchroman-6-sulphonyl
Pro: L-proline
Ser: L-serine
tBu: tert-butyl
TFA: trifluoroacetic acid
TFMSA: trifluoromethanesulphonic acid
Thr: L-threonine
Tos: tosyl
Trt: trityl
Tyr: L-tyrosine The invention is illustrated below by means of the following non-limiting examples.

EXAMPLE 1

Incorporation of an internal standard. Obtaining BocIle-pMBHa.

1.658 g (6.9 mmoles) of BocIle are incorporated on 4 g of p-methylbenzhydrilamine resin of 0.69 mmoles/g resin as an internal standard by means of the synthesis programme described below:

| Step | Reagent | Repetitions | Time |
| --- | --- | --- | --- |
| 1 | TFA 40% | 1 | 2' |
| 2 | TFA 40% | 1 | 20' |
| 3 | DCM | 5 | 1' |
| 4 | DIEA 5% | 3 | 2' |
| 5 | DCM | 5 | 1' |
| 6 | Boc aa | – | + |
| 7 | HOBt | – | + |
| 8 | DIPCDI | – | 40' |
| 9 | DCM | 5 | 1' |
| 10 | check with ninhydrin, if + return to 6, if – continue | | |
| 11 | DCM | 5 | 1' |
| 12 | TFA 40% | 1 | 2' |
| 13 | TFA 40% | 1 | 20' |
| 14 | DCM | 5 | 1' |
| 15 | DIEA 5% | 3 | 2' |
| 16 | DCM | 5 | 1' |

EXAMPLE 2

Incorporation of the Riniker handle. Obtaining 4(4-hydroxymethyl-3-methoxyphenoxy)butyramide-Ile-pMBHA.

There then follows the incorporation of 4(4-hydroxymethyl-3-methoxyphenoxy)butyric acid, also known as the Riniker handle (HMPB). This is carried out by reacting 4 g of the resin (fNH$_2$0.69 mmoles/g of resin), after it has been previously functionalized with the internal standard, with 1 g (4.14 Moles of, 1.5 equivalents) of 4(4-hydroxymethyl-3-methoxyphenoxy) butyric acid, 0.62 g (4.14 mmoles, 1.5 equivalents) of HOBt and 641 µl (4.14 mmoles, 1.5 equivalents) using DMF as the solvent. The reaction time is 90'. After this time has elapsed, the resin is washed five times with DCM and the Kaiser is used to check that there are no free amines. If there are, the coupling process must be repeated.

EXAMPLE 3

Incorporation of the first amino acid. Obtaining Fmoc Gly-Riniker handle-Ile-pMBHA. Riniker handle-Ile-pMBHA.

The incorporation of the first amino acid, in this case glycine, implies the formation of an ester-type link between the handle and the Fmoc Gly derivative. For this kind of incorporation the resin is reacted with 4.1 g (5 equivalents) of Fmoc Gly in the presence of 168 mg (0.5 equivalents) of DMAP and 2.094 ml (5 equivalents) of DIPCDI in DMF for 90". Once the reaction is complete the resin is washed five times with DMF. An amino acid analysis of an acid hydrolysis of the resin .gives the ratio of the Ile amino acid (internal standard) and the first amino acid Gly. In this way the real functionalization of the resin is known, normally varying between 0.35–0.69 mmoles/g.

EXAMPLE 4

Incorporation of the remaining amino acids. Obtaining BocCys(Acm)-Ser(tBu)-Asn-Leu-Ser(tBu)-Thr(tBu)-Cys(Trt)-Val-Leu-Gly-Riniker handle-Ile-pMBHA (fragment 4).

The incorporation of the remaining amino acids is carried out by following a synthesis programme such as the one described below:

| Step | Reagent | Repetitions | Time |
|------|---------|-------------|------|
| 1 | DMF | 5 | 1' |
| 2 | pip/DMF 20% | 1 | 1' |
| 3 | pip/DMF 20% | 1 | 5' |
| 4 | DMF | 5 | 1' |
| 5 | Fmoc aa | — | + |
| 6 | HOBt | — | + |
| 7 | DIPCDI | — | 40' |
| 8 | DMF | 5 | 1' | check with ninhydrin, if+return to 5, if—continue with step 1 and the next amino acid.

In order to evaluate the synthetic purity of the totally deprotected peptide 1–10, 20 mg of BocCys(Acm)-Ser(tBu)-Asn-Leu-Ser(tBu)-Thr(tBu)-Cys(Trt)-Val-Leu-Gly -Riniker handle-Ile-pMBHA are treated with 900 µl of TFA, 50 µl of thioanisole, 30 µl of EDT and 20 µl of anisole for 2 hours at room temperature in a reactor provided with a filter plate. The filtrate is collected in a tube with cold, dry diethyl ether. The precipitation of the free peptide is observed and after centrifuging the floating material is decanted. The pellet is resuspended once again in cold, dry ether to eliminate the scavengers (EDT, thioanisole, anisole). This operation is repeated five times. Afterwards the pellet is dried and then dissolved in 1 ml of 10% acetic acid solution. 40 µl of the peptide solution are injected into HPLC with a gradient of 5–85% B, where A: $H_2O$ 0.045% TFA and B: $CH_3CN$ 0.035% TFA, Vydac C18 5 µm, 25×0.46 cm. An amino acid analysis of a hydrolysis of the peptide-resin at 150° C. for 3 hours with a mixture of HCl/propanoic acid gives the following composition Asp 1.01 (1), Thr 0.8 (1), Ser 1.6 (2), Gly 1.2 (1), Ile 1.5–1 (1), Leu 1.99 (2), Val 0.89 (1).

EXAMPLE 5

Breaking the peptide 1–10 from the resin. Obtaining

BocCys(Acm)—Ser(tBu)—Asn—Leu—Ser(tBu)—Thr(tBu)—Cys(Trt)—Val—Leu—Gly—OH  (fragment 3) or

BocCys—Ser(tBu)—Asn—Leu—Ser(tBu)—Thr(tBu)—Cys—Val—Leu—Gly—OH  (fragment 2).

This treatment can be carried out either before or after the oxidation process, as indicated in diagram 4. The subsequent treatment differs slightly in each case. In order to break the peptide-resin link before oxidation, route A must be followed. To break the link after oxidation route B must be followed.

Route A: The peptide-resin is treated with 1% TFA in DCM 4 or 5 times at intervals of 15 minutes, hexane is added to the filtrates and it is evaporated in a rotavapour. A white solid is obtained.

Route B: The peptide-resin is treated with 1% TFA in DCM 4 or 5 times at intervals of 15 minutes. After each filtration the solution is neutralised with twice as much pyridine as the amount of TFA which the solution contains. The total of the filtrates is concentrated to 20% of its initial volume in the rotavapour. The concentrated peptide solution is added to cold diethyl ether. The white precipitate obtained is separated by centrifuging. The solid is resuspended in diethyl ether and centrifuged once again. This operation is repeated three more times. Finally the solid obtained is dried.

EXAMPLE 6

Formation of disulphide bridge on resin. Obtaining

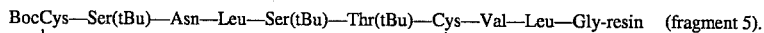
BocCys—Ser(tBu)—Asn—Leu—Ser(tBu)—Thr(tBu)—Cys—Val—Leu—Gly-resin  (fragment 5).

The deprotection and simultaneous formation of disulphide bridge links on the resin BocCys(Acm) Ser(tBu)-Asn-Leu-Ser(tBu)-Thr(tBu)-Cys(Trt)-Val-Leu-Gly-handle-(R) is carried out in DCM/MeOH/$H_2O$ (6:2.5:0.42) with two $I_2$ equivalents over two intervals of 30 minutes.

EXAMPLE 7

Formation of disulphide bridge in solution. Obtaining

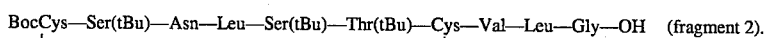
BocCys—Ser(tBu)—Asn—Leu—Ser(tBu)—Thr(tBu)—Cys—Val—Leu—Gly—OH  (fragment 2).

The oxidization of the peptide Boc Cys(Acm)-Ser(tBu)-Asn-Leu-Ser(tBu)-Thr(tBu)-Cys(Trt)-Val-Leu-Oly-OH is carried out in DCM/MeOH/$H_2O$ (6:2.5:0.42) with 4 $I_2$ equivalents for 10 minutes. Afterwards the reaction mixture is washed with a solution of sodium thiosulphate 0.1N adding $CHCl_3$. The organic phase is washed with water, dried with sodium sulphate and evaporated to dryness. A white solid is obtained.

EXAMPLE 8

Incorporation of the Fmoc AM handle on Boc-Ile-pMBHa. Obtaining p-[(R,S)-a-[1-(9H-fluoren-9-yl)methoxy-formamide]-2,4-dimethoxy benzyl]-phenoxy acetamide-Ile pMBHA.

There then follows the incorporation of p-[(R,S)-a-[1(9H-fluoren-9-yl)methoxy-formamide]-2,4-dimethoxy benzyl]-phenoxy acetic acid (Fmoc-AM). This is carried out by reacting 4 g of the resin (0.69 mmoles/g of resin), after it has been previously functionalized with the internal standard (following the protocol described in example 1), with 2.23 g (4.14 mmoles, 1.5 equivalents) of p-phenoxy-acetic acid, 0.62 g (4.14 mmoles, 1.5 equivalents) of HOBt and 641 μl (4.14 mmoles, 1.5 equivalents) using DMF as the solvent. The reaction time is 90'. After this time has elapsed, the resin is washed five times with DCM and the Kaiser test is used to check that there are no free amines. If there are, the coupling process must be repeated.

EXAMPLE 9

Incorporation of the Fmoc PAL handle on Boc-Ile-pMBHa. Obtaining 4[1-(9H-fluoren-9-yl)methoxy-formamide] methyl -3.5-dimethoxyphenoxyvaleriamide-Ile pMBHA.

There then follows the incorporation of 4[1-(9H -fluoren-9-yl)methoxy-formamide]methyl-3,5-dimethoxyphenoxyvaleric acid (Fmoc-PAL). This is carried out by reacting 4 g of the resin (0.69 mmoles/g of resin), after it has been previously functionalized with the internal standard (following the protocol described in example 1), with 1.89 g (4,14mmoles, 1.5 equivalents) of 4[1-(9H -fluoren-9-yl)methoxy-formamide] methyl-3,5-dimethoxyphenoxyvaleric acid, 0.62 g (4.14 mmoles, 1.5 equivalents) of HOBt and 641 μl (4.14 mmoles, 1.5 equivalents) using DMF as the solvent. The reaction time is 90'. After this time has elapsed, the resin is washed five times with DCM and the Kaiser is used to check that there are no free amines. If there are,, the coupling process must be repeated.

EXAMPLE 10

Incorporation of the remaining amino acids. Obtaining Fmoc Lys(Boc)-Leu-Ser(tBu)-Gln-Glu(tBu)-Leu-His(Trt)-Lys (Boc)-Leu-Gln-Thr(tBu)-Tyr(tBu)-Pro-Arg(Pmc)-Thr(tBu)-Asn -Thr(tBu)-Gly-Ser(tBu)-Gly-Thr(tBu)-Pro-AM-Ile-PMBHA.

The incorporation of the remaining amino acids is carried out by following a synthesis programme such as the one described below:

| Step | Reagent | Repetitions | Time |
| --- | --- | --- | --- |
| 1 | DMF | 5 | 1' |
| 2 | pip/DMF 20% | 1 | 1' |
| 3 | pip/DMF 20% | 1 | 5' |
| 4 | DMF | 5 | 1' |
| 5 | Fmoc aa | — | + |
| 6 | HOBt | — | + |
| 7 | DIPCDI | — | 40' |
| 8 | DMF | 5 | 1' | check with ninhydrin, if+return to 5, if–continue with step 1 and the next amino acid.

In order to evaluate the synthetic purity of the totally deprotected peptide 11–32, 20 mg of Fmoc Lys(Boc) -Leu-Ser(tBu)-Gln-Glu(tBu)-Leu-His(Trt)-Lys(Boc)-Leu-Gln -Thr(tBu)-Pro-Arg(Pmc)-Thr(tBu)-Gly-Ser(tBu)-Gly-Thr(tBu) -Pro-AM-Ile-pMBHA (fragment 1 are treated with 900 μl of TFA, 50 μl of thioanisole, 30 μl of EDT and 20 μl of anisole for 2 hours at room temperature in a reactor provided with a filter plate. The filtrate is collected in a tube with cold, dry diethyl ether. The precipitation of the free peptide is observed and after centrifuging the floating material is decanted. The pellet is resuspended once again in cold, dry ether to eliminate the scavengers (EDT, thioanisole, anisole). This operation is repeated five times. Afterwards the pellet is dried and then dissolved in 1 ml of a solution of 10% acetic acid. 40 μl of the peptide solution are injected into HPLC with a gradient of 5–85% B, where A: $H_2O$ 0.045% TFA and B: CH CN 0.035% TFA, Vydac C 18 5 μm, 25×0.46 cm. An amino acid analysis of a hydrolysis of the peptide-resin at 150° C. for 3 hours with a mixture of HCl/propanoic acid gives the following composition Asp 1.06 (1), Thr 4.0 (4), Ser 2.0 (2), Glu 3.01 (3), Gly 2.2 (2), Pro 1.98 (2), Ile 0.9 (1), Leu 3.0 (3), Tyr 0.8 (1), His 0.92 (1), Lys 1.8 (2), Arg 1.03 (1).

EXAMPLE 11

Incorporation of fragment 2 on the peptide-resin of fragment 1. Obtaining Boc Cis-Ser(tBu)-Asn-Leu-Ser(tBu) -Thr(tBu)-Cis-Val-Leu-Gly-Lys(Boc)-Leu-Ser(tBu)-Gln -Glu(tBu)-Leu-His(Trt)-Lys(Boc)-Leu-Gln-Thr(tBu)- Tyr(tBu) -Pro-Arg(Pmc)-Thr(tBu)-Asn-Thr(tBu)-Gly-Ser(tBu)-Gly -Thr(tBu)-Pro-AM-Ile-pMBHA (fragment 6).

1.58 g of the peptide-resin 11–32 are treated with piperidine/DMF for 3 minutes. The operation is repeated two more times and the resin is then washed 5 times for 1 minute with DMF. 315 mg (2.5 equivalents) of HBTU and 124 mg (2.5 equivalents) of HOBT dissolved in DMF are added to the resin, forming the most homogeneous mass possible therewith. 1.05 g (2.5 equivalents) of the peptide 1–10, its N-terminal end and side chains being totally protected by the disulphide bridge already formed, is dissolved in the minimum quantity possible of DMF and added to the resin. Finally 296 μl (5 equivalents) of DIEA are added. The resin is shaken well until it is homogeneous. The reaction acquires an orange colour. One hour and 30 minutes later the Kaiser test on one aliquot, part of the resin gives a negative result and the incorporation reaction can be considered complete. The resin is filtered and washed repeatedly with DMF.

EXAMPLE 12

Breaking the resin and deprotection of the peptide 1–32. Obtaining

Cis—Ser—Asn—Leu—Ser—Thr—Cis—Val—Leu—Gly—Lys—Leu—Ser—Gln—Glu—Leu—His—Lys—Leu—Gln—Thr—Tyr—Pro—Arg—Thr—Asn—Thr—Gly—Ser—Gly—Thr—Pro—NH$_2$ (salmon calcitonin).
The peptide-resin 1.32

Boc Cis—Ser(tBu)—Asn—Leu—Ser(tBu)—Thr(tBu)—Cis—Val—Leu—Glu—Lys(Boc)—Leu—Ser(tBu)—Gln—Glu(tBu)—Leu—His(Trt)—Lys(Boc)—Leu—Gln—Thr(tBu)—Tyr(tBu)—Pro—Arg(Pmc)—Thr(tBu)—Asn—Thr(tBu)—Gly—Ser(tBu)—Gly—Thr(tBu)—Pro-AM-Ile-pMBHA when completely dry is treated with TFA/DCM/anisole (95:3:2) for 2 hours at room temperature. Afterwards the filtrate is poured onto 100 ml of cold, dry diethyl ether. The white precipitate obtained is separated by centrifuging. The solid is resuspended In diethyl ether and centrifuged again. This operation is carried out five more times. Finally the solid obtained is dried. The solid dissolved in 10% AcOH is purified by an HPLC preparation with a gradient of 5–65%

B, where A: H₂O 0.05% TFA and B: CH₃CN 0.05% TFA, Vydac C 18 15–20 μm, 25×1 cm.

We claim:

1. A procedure for obtaining salmon calcitonin and its pharmaceutically acceptable acid addition salts or complexes thereof, by means of solid phase synthesis on polymeric supports and with the intervention of Fmoc and/or tBu protective groups combined with a convergent strategy, comprising the steps of:

(a) condensing fragment 1 with fragment 2, wherein fragment 1 consists of the docosapeptide corresponding to the carboxamide end of the salmon calcitonin sequence, conveniently protected and anchored on resin:

Lys(Boc)—Leu—Ser(tBu)—Gln—Glu(tBu)—Leu—His(Trt)—

Lys(Boc)—Leu—Gln—Thr(tBu)—Tyr(tBu)—Pro—Arg(Pmc)—

Thr(tBu)—Asn—Thr(tBu)—Gly—Ser(tBu)—Gly—Thr(tBu)—Pro—Ⓡ

Fragment 1 (SEQ ID NO: 1)

wherein —Ⓡ has the following structure

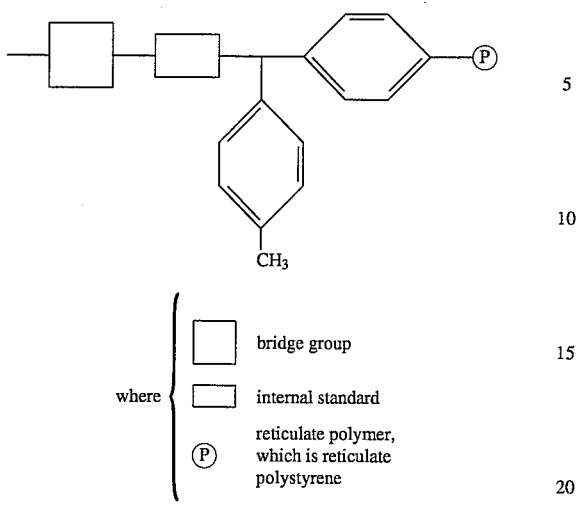

where
- ☐ bridge group
- ☐ internal standard
- Ⓟ reticulate polymer, which is reticulate polystyrene and wherein fragment 2 is a decapeptide corresponding to the amino end of the salmon calcitonin sequence, conveniently protected and with a disulphide bridge formed between the two cysteines:

Boc—Cys—Ser(tBu)—Asn—Leu—Ser(tBu)—Thr(tBu)—Cys—Val—
    |_____|
                                          —Leu—Gly—OH

Fragment 2 (SEQ ID NO: 2)

(b) subjecting the resulting peptide-resin, which corresponds to fragment 6:

Boc—Cys—Ser(tBu)—Asn—Leu—Ser(tBu)—Thr(tBu)—Cys—
    |_____|

Val—Leu—Gly—Lys(Boc)—Leu—Ser(tBu)—Gln—

Glu(tBu)—Leu—His(Trt)—Lys(Boc)—Leu—Gln—

Thr(tBu)—Tyr(tBu)—Pro—Arg(Pmc)—Thr(tBu)—Asn—

Thr(tBu)—Gly—Ser(tBu)—Gly—Thr(tBu)—Pro—Ⓡ

Fragment 6 to a simultaneous treatment of deprotection of the amino acid side chains and cleavage from the resin to obtain the peptide which, after purification, yields substantially pure salmon calcitonin.

2. A procedure according to claim 1, characterized in that the cleavage fragment 6 (SEQ ID NO:6) from the resin is carried by treatment with acid in the presence of carbocation sequestering agents.

3. A procedure according to claim 1 characterized in that alternatively in step (a) fragment 1(SEQ ID NO:1) is condensed with the precursor of fragment 2, (SEQ ID NO:2) corresponding to fragment 3(SEQ ID NO:3):

<u>Boc</u>—Cys(Acm)—Ser(tBu)—Asn—Leu—Ser(tBu)—Thr(tBu)—Cys(Trt)—Val—Leu—Gly—OH

Fragment 3 to obtain the peptide-resin corresponding to fragment 7(SEQ ID NO:7):

Boc—Cys(Acm)—Ser(tBu)—Asn—Leu—Ser(tBu)—Thr(tBu)—Cys(Trt)—Val—Leu—Gly—Lys(Boc)—Leu—Ser(tBu)—Gln—Glu(tBu)—Leu—His(Trt)—Lys(Boc)—Leu—Gln—Thr(tBu)—Tyr(tBu)—Pro—Arg(Pmc)—Thr(tBu)—Asn—Thr(tBu)—Gly—Ser(tBu)—Gly—Thr(tBu)—Pro—Ⓡ

Fragment 7 which is selectively oxidized while bound to a solid phase support to form a disulphide bridge between the two cysteines in order to obtain fragment 6 (SEQ ID NO:6) which is then subjected to concommitant amino acid side chain deprotection and cleavage from the resin, followed by purification of the resulting peptide to yield chemically pure salmon calcitonin.

4. A procedure according to claim 3 characterized in that the oxidation of fragment 7(SEQ ID NO: 7) to obtain fragment 6(SEQ ID NO:6) is carried out with $I_2$.

5. A procedure according to claim 3, characterized in that fragment 1 is obtained from pMBHA resin by incorporating the internal standard and the bridge group between the resin and the sequence of amino acids, this being followed by linear synthesis, residue by residue, until the 22 amino acids of fragment 1 have been incorporated.

6. A procedure according to claim 1 characterized in that fragment 1 (SEQ ID NO:1) is obtained from pMBHA resin by incorporating-the internal standard and the bridge group between the resin and the sequence of amino acids, this being followed by linear synthesis, residue by residue, until the 22 amino acids of fragment 1 have been incorporated.

7. A procedure according to claim 6 characterized in that PAL or AM are used as the bridge group and the amino acid Ile is used as the internal standard.

8. A procedure according to claim 6 characterized in that during the linear synthesis of each of the 22 amino acids the protective group Fmoc is used for the amino end in all cases and for the side chains Lys, Set, Thr, Tyr, Arg, Glu, His, Gln and Asn the protective groups indicated for said what is in the formula of fragment 1 (SEQ ID NO:1) illustrated above are used.

9. A procedure according to claim 1 characterized in that fragment 2 (SEQ ID NO:2) obtained from pNBHA resin by incorporating the group Ile as the internal standard and the group HMPB as the bridge group between the resin and the sequence of amino acids, this being followed by linear synthesis, residue by residue, until the 10 amino acids have been incorporated, using the protective group Fmoc for the amino end in all cases except the last amino acid, for which the Boc group is used, and for the side chains Ser, Thr, Cys and Asn using the protective groups indicated for said chains in the formula of the resulting fragment 4(SEQ ID NO:4)

Boc—Cys(Acm)—Ser(tBu)—Asn—Leu—Ser(tBu)—Thr(tBu)—Cys(Trt)—Val—Leu—Gly—Ⓡ

Fragment 4 which, after the simultaneous deprotection/oxidation with iodine of the two protective groups of the cysteine residues leads to fragment 5 (SEQ ID NO: 5):

Boc—Cys—Ser(tBu)—Asn—Leu—Ser(tBu)—Thr(tBu)—Cys—Val—Leu—Gly—Ⓡ
       |_____|

Fragment 5 which, after the cleavage of the peptide-resin link, results in fragment 2 (SEQ ID NO:2).

10. A procedure according to claim 1 characterized in that alternatively fragment 4 (SEQ ID NO:4) is subjected to the breaking of the peptide-resin link to obtain fragment 3 (SEQ ID NO:3):

Boc—Cys(Acm)—Ser(tBu)—Asn—Leu—Ser(tBu)—Thr(tBu)—Cys(Trt)—Val—Leu—Gly

Fragment 3 which is oxidized with iodine to lead to fragment 2 (SEQ ID NO:2).

11. A peptide fragment for use in the synthesis of salmon calcitonin characterized in that it consists of the following sequence and structure, protected and anchored on resin:

Lys(Boc)—Leu—Ser(tBu)—Gln—Glu(tBu)—Leu—His(Trt)—Lys(Boc)—Leu—Gln—Thr(tBu)—
Tyr(tBu)—Pro—Arg(Pmc)—Thr(tBu)—Asn—Thr(tBu)—Gly—Ser(tBu)—Gly—Thr(tBu)—Pro—Ⓡ

Fragment 1 (SEQ ID NO: 1)

where Boc, tBu, Trt and Pmc are the protective groups for the amino acid residue indicated and Ⓡ is

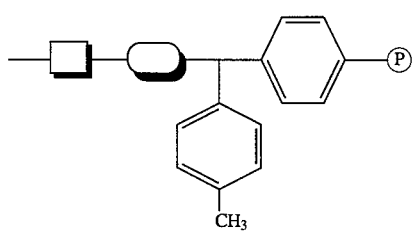

where
- □ bridge group
- ⬭ internal standard
- Ⓟ reticulate polymer, preferably reticulate polystyrene 12. A peptide fragment for use in the synthesis of salmon calcitonin characterized in that is consists of the following sequence and structure, protected and anchored on resin (SEQ ID NO:2).

Boc—Cys—Ser(tBu)—Asn—Leu—Ser(tBu)—Thr(tBu)—Cys—Val—Leu—Gly—Ⓡ
       |_____| where Boc and tBu are the protective groups for the amino acid residue indicated and Ⓡ is defined as in claim 11.

13. A peptide fragment for use in the synthesis of salmon calcitonin characterized in that it consists of the following sequence and structure, protected and anchored on resin:

Boc—Cys—Ser(tBu)—Asn—Leu—Ser(tBu)—Thr(tBu)—Cys—Val—Leu—Gly—Lys(Boc)—
Leu—Ser(tBu)—Gln—Glu(tBu)—Leu—His(Trt)—Lys(Boc)—Leu—Gln—Thr(tBu)—Tyr(tBu)—
Pro—Arg(Pmc)—Thr(tBu)—Asn—Thr(tBu)—Gly—Ser(tBu)—Gly—Thr(tBu)—Pro—Ⓡ

Fragment 6 (SEQ ID NO: 6)

where Boc, tBu, Trt and Pmc are the protective groups for the amino acid residue indicated and Ⓡ is defined as in claim 11.

* * * * *